(12) United States Patent  (10) Patent No.: US 7,390,460 B2
Osawa et al.  (45) Date of Patent: Jun. 24, 2008

(54) CONTROL DEVICE FOR AUTOMATIC LIQUID HANDLING SYSTEM

(75) Inventors: Hidetaka Osawa, Hitachinaka (JP); Hiroatsu Toi, Hitachinaka (JP); Kenji Yamada, Hitachinaka (JP); Tadashi Ohkawara, Hitachinaka (JP)

(73) Assignee: Hitachi Koki Co., Ltd. (JP)

( * ) Notice: Subject to any disclaimer, the term of this patent is extended or adjusted under 35 U.S.C. 154(b) by 933 days.

(21) Appl. No.: 10/714,891

(22) Filed: Nov. 18, 2003

(65) Prior Publication Data

US 2004/0096366 A1 May 20, 2004

(30) Foreign Application Priority Data

Nov. 18, 2002 (JP) ............................ P2002-334432

(51) Int. Cl.
*G01N 21/00* (2006.01)
(52) U.S. Cl. .............................. 422/65; 422/63; 422/64; 422/67; 422/73; 422/99; 422/100; 422/101; 436/180
(58) Field of Classification Search ............. 422/63–65, 422/99–101, 67, 73; 73/864.25; 436/180
See application file for complete search history.

(56) References Cited

U.S. PATENT DOCUMENTS 5,670,113 A * 9/1997 Akong et al. ................... 422/63
6,006,800 A * 12/1999 Nakano ....................... 141/130

FOREIGN PATENT DOCUMENTS

| JP | 5-232124 | 9/1993 |
| JP | 8-271528 | 10/1996 |
| JP | 2000-83650 | 3/2000 |

* cited by examiner

*Primary Examiner*—Jill Warden
*Assistant Examiner*—Jyoti Nagpaul

(57) ABSTRACT

In reagent reaction experiments using microplates, a desired period of time can be set for determining the time to introduce a reaction stop solution after introduction of a reagent. The set time is measured starting from the introduction of the reagent and the reaction stop solution is introduced immediately after expiration of the set time. A control device for an automatic liquid handling system having the above-described reaction time managing feature is also provided with a self-diagnosing function that is capable of determining whether scheduled processes are executable or not during the time set before execution of the processes and informing an operator of the results of determination.

16 Claims, 5 Drawing Sheets

FIG.6

| PROCESS NUMBER | PROCESS NAME | PROCESS (CONDITIONS) | TIME REQUIRED (SECONDS) |
|---|---|---|---|
| 1 | DISPENSE | ROW 1 COLUMNS A TO E DISPENSE 144 µl REAGENT 1 IN ↑ DIRECTION | 62 |
| 2 | DISPENSE | FROM COLUMN A ROWS 2 TO 12 TO COLUMN E DISPENSE 100 µl REAGENT 2 IN → DIRECTION | 178 |
| 3 | DILUTE | PIPETTING 5 TIMES FROM ROW 1 COLUMNS A TO E TO ROW 8 DILUTING DISPENSE 50 µl IN ↑ DIRECTION | 117 |
| 4 | INCUBATE | AT 37°C FOR 10 MINUTES | 600 |
| 5 | DISPENSE | COLUMN A ROWS 1 TO 12 DISPENSE 100 µl REAGENT 3 IN → DIRECTION | 50 |
| 6 | DISPENSE | COLUMN B ROWS 1 TO 12 DISPENSE 100 µl REAGENT 4 IN → DIRECTION | 50 |
| 7 | DISPENSE | COLUMN C ROWS 1 TO 12 DISPENSE 100 µl REAGENT 5 IN → DIRECTION | 50 |
| 8 | DISPENSE | COLUMN D ROWS 1 TO 12 DISPENSE 100 µl REAGENT 6 IN → DIRECTION | 50 |
| 9 | DISPENSE | COLUMN E ROWS 1 TO 12 DISPENSE 100 µl REAGENT 7 IN → DIRECTION | 50 |
| 10 | INCUBATE → DISPENSE STOP SOLUTION | INCUBATE AT 37°C TIME TO DISPENSING STOP SOLUTION 30 MINUTES | 1800 |
| | | FROM COLUMN A ROWS 1 TO 12 TO COLUMN E DISPENSE 75 µl REAGENT 8 IN → DIRECTION | 220 |

CONTROL DEVICE FOR AUTOMATIC LIQUID HANDLING SYSTEM

BACKGROUND OF THE INVENTION

1. Field of the Invention

The present invention relates to the control device for an automatic liquid handling system that manages reaction time of reagent or enzymes that are used in drug metabolic experiments.

2. Description of Related Art

In the development of new drugs, drug metabolic experiments are frequently carried out, and each experiment is involved with a large amount of work. It is therefore essential to reduce mistakes caused by human error. To this end, human operations tend to be replaced by automatic mechanical operations.

It is important to manage a reagent reaction time in drug metabolic experiments. Japanese Patent Application Publication No. 2000-83650 discloses an automatic test apparatus used in conducting metabolic experiments. The apparatus includes a three-dimensionally movable robot having a tip end on which a single dispensing probe is mounted. With this apparatus, a solution of specimen is dripped into a reaction stop solution stored in a vial after expiration of a predetermined period of time during which reaction occurs. This period of time is specifically determined depending on the specimen subject to the experiment. Japanese Patent Application Publication No. 2000-83650 discloses setting an enzyme reaction time to be 30 minutes, 60 minutes, 120 minutes as examples. Selection of the reaction time is carried out by a program installed in a control device.

The above-described apparatus is disadvantageous in that with a single dispensing probe, a number of experiments cannot be performed at high speed. To resolve the disadvantage, recent tendency is to use microplates having wells formed in an n-by-m matrix instead of vials. The use of microplates reduces costs and the quantity of reagent. In an automatic liquid handling system using the microplates, a large number of processings involved in a drug metabolic experiment can be performed at high speed.

However, accurate and reliable experiment cannot be performed with the automatic liquid handling system using the microplates. Despite the fact that a small quantity of reagent shortens a reaction time, reaction time in different rows of the wells on the microplate varies due to variation in robot operation time, time needed for attaching and detaching the dispensing tips to and from the robot, and a work time needed for an operator to temporarily stop the robot to supplement the reagent. The above-described disadvantages are particularly fatal in the case where a desired reaction time is short or a reagent reaction time expires during the robot is executing another process.

Further problem arises such that when the system is restarted due to occurrence of operational errors or accidental power down of the system, execution of the outstanding process may be finished before or after expiration of a desired reaction time. In such cases, the results of experiment are not available and so the experiment per se is vain.

SUMMARY OF THE INVENTION

In view of the foregoing, it is an object of the invention to provide a control device for an automatic liquid handling system capable of measuring a predetermined period of time starting from introduction of a reagent and introducing a reaction stop solution immediately after expiration of the predetermined period of time.

Another object of the invention is to provide a control device for an automatic liquid handling system having a self-diagnosing function that is capable of determining whether scheduled processes are executable or not during a time set in advance before execution of the processes and informing an operator of the results of determination.

Still another object of the invention is to provide a control device for an automatic liquid handling system capable of informing the operator of an accurate reaction time even if the system is temporarily stopped for some reasons.

In accordance with the invention, there is provided an automatic liquid handling system that includes a dispensing tip container, a reagent container, a microplate formed with a plurality of wells, and a dispensing head. The dispensing tip container has a plurality of holding portions for holding dispensing tips. The reagent container holds one or more reagents. The dispensing head has attachment portions to which at least one dispensing tip is attached. When one or more dispensing tips are attached to the attachment portions, the dispensing head is capable of performing sucking and expelling operations. Specifically, the dispensing head can suck the reagent into the dispensing tips from the reagent container, expel the reagent out from the dispensing tips, and drip the reagent into the wells of the microplate. Also, the dispensing head can suck the liquid in the specified wells of the microplate and drip the sucked liquid into another specified wells. Moving means is also provided for moving the dispensing head. The liquid handling system also includes a control device that controls the sucking and expelling operations performed by the dispensing head and also controls the moving means to control movements of the dispensing head. The control device has input means for inputting one or more processes to be executed by the dispensing head. Time measuring means is provided for measuring time starting from dripping the reagent into selected wells on the microplate by the expelling operation performed by the dispensing head.

According to another aspect of the invention, there is further provided self-diagnosing means for simulating time to execute the one or more processes to be executed by the dispensing head and determining whether the one or more processes are executable in the time set by time setting means. In this case, the time measuring means is not essential to the invention.

BRIEF DESCRIPTION OF THE DRAWINGS

In the drawings:

FIG. 6 shows an example of a process table for a metabolic experiment.

DETAILED DESCRIPTION OF THE PREFERRED EMBODIMENTS

Figure 1:
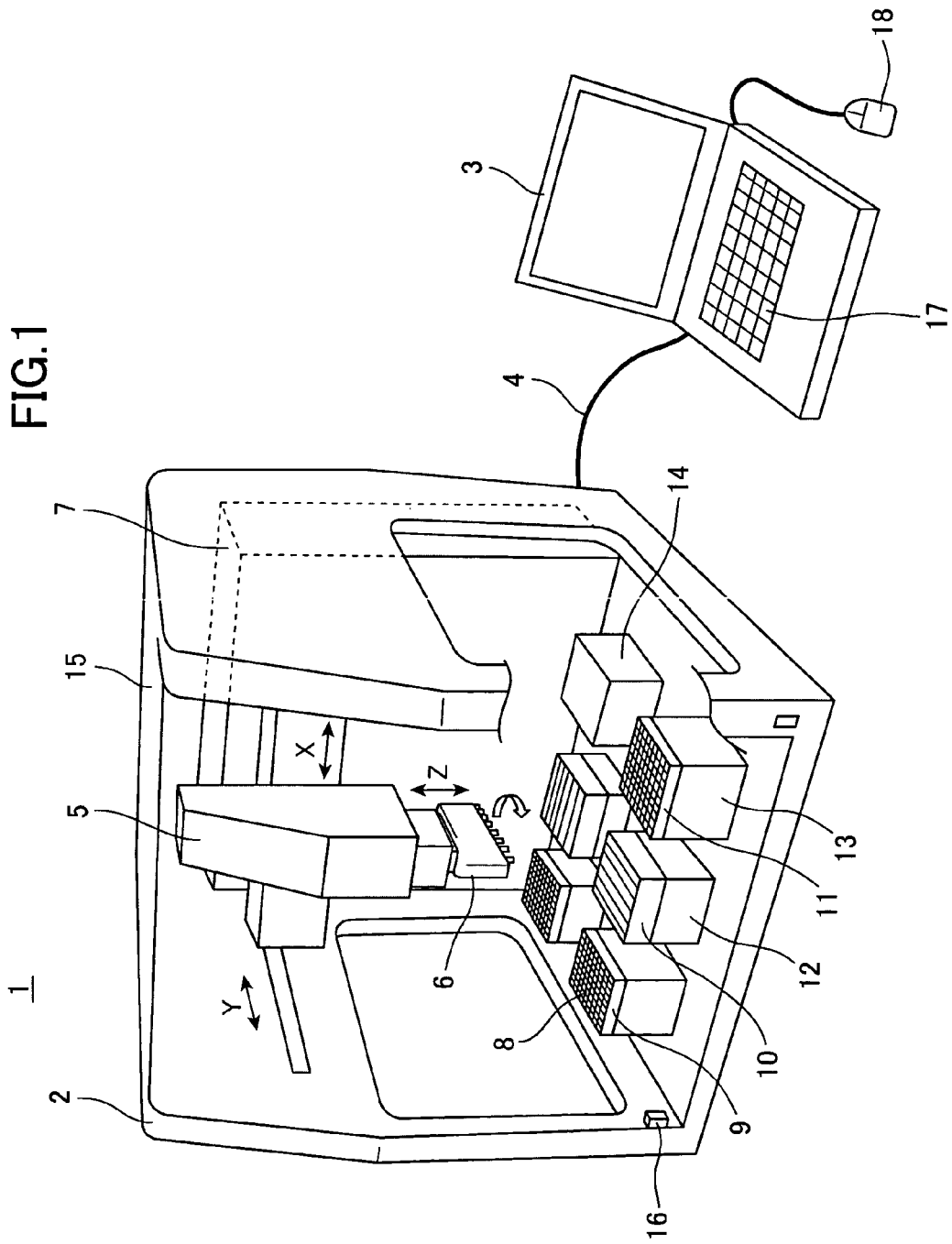
FIG. 1 is a perspective view of an automatic liquid handling system according to an embodiment of the present invention.

A preferred embodiment of the present invention will be described with reference to the drawings. FIG. 1 shows an automatic liquid handling system 1 according to a preferred embodiment of the present invention. The automatic liquid handling system 1 includes a main body 2 and a control device 3 connected together with a communication cable 4 such as a LAN (Local Area Network) cable. A general-purpose personal computer is used as the control device 3. The main body 2 of the automatic liquid handling system 1 includes a robot 5 capable of moving and stopping in 3D space, a dispensing head 6 provided at a tip end of the robot 5, and a driving circuit 7 for driving the main body 2 based upon conditions input into the control device 3.

The robot 5 has three orthogonal axes, X, Y, and Z, and is capable of being moved by stepper motors (not shown) to a predetermined position. Servo-motors can be used instead of the stepper motors. A plurality of dispensing tips 8 aligned at an equi-pitch can be removably attached to the dispensing head 6. The dispensing head 6 to which a dispensing tip 8 is attached can suck or expel liquid. For example, the dispensing head 6 described above can hold twelve syringes (not shown in the drawings) which are driven by one stepper motor. The spacing between syringes is 9 mm pitch, the same as the spacing between wells of a microplate 11. When a dispensing tip 8 is attached to the dispensing head 6, liquid can be sucked in or expelled out by driving the syringe.

Arranged beneath the dispensing head 6 of the robot 5 are a dispensing tip container 9, reagent containers 10, the microplate 11, and a disposal container 14. The dispensing tip container 9 has dispensing tip holding portions arranged at a pitch same as the well pitch of the microplate 11, that is, 9 mm pitch. The reagent container 10 holds reagent that is used in an experiment. The microplate 11 holds a specimen subject to the experiment. The disposal container 14 holds used dispensing tips 8. A plurality of wells is formed in the microplate 11 in an n-by-m matrix arrangement. For example, an 8-by-12 arrangement would have 96 wells. Also, the dispensing head 6 is capable of swiveling through 90 degrees, so that it is capable of dispensing to the microplate 11 in the two orthogonal directions.

A cover 15 is provided to the ceiling part and the side faces of the main body 2 of the automatic liquid handling system 1. Also, a door (not shown in the drawings) is provided to the front of the main body 2 of the automatic liquid handling system 1. The door is opened when preparing reagent or test specimens, and during execution of the experiment the door is closed and the automatic liquid handling system is operated. For the sake of safety of the operators, a reed switch 16 is provided to detect, whether the door is open or closed. When the door is open, the contacts of the reed switch are rendered open, causing the electrical power lines to the motors to interrupt and thus the robot to stop.

Figure 2:
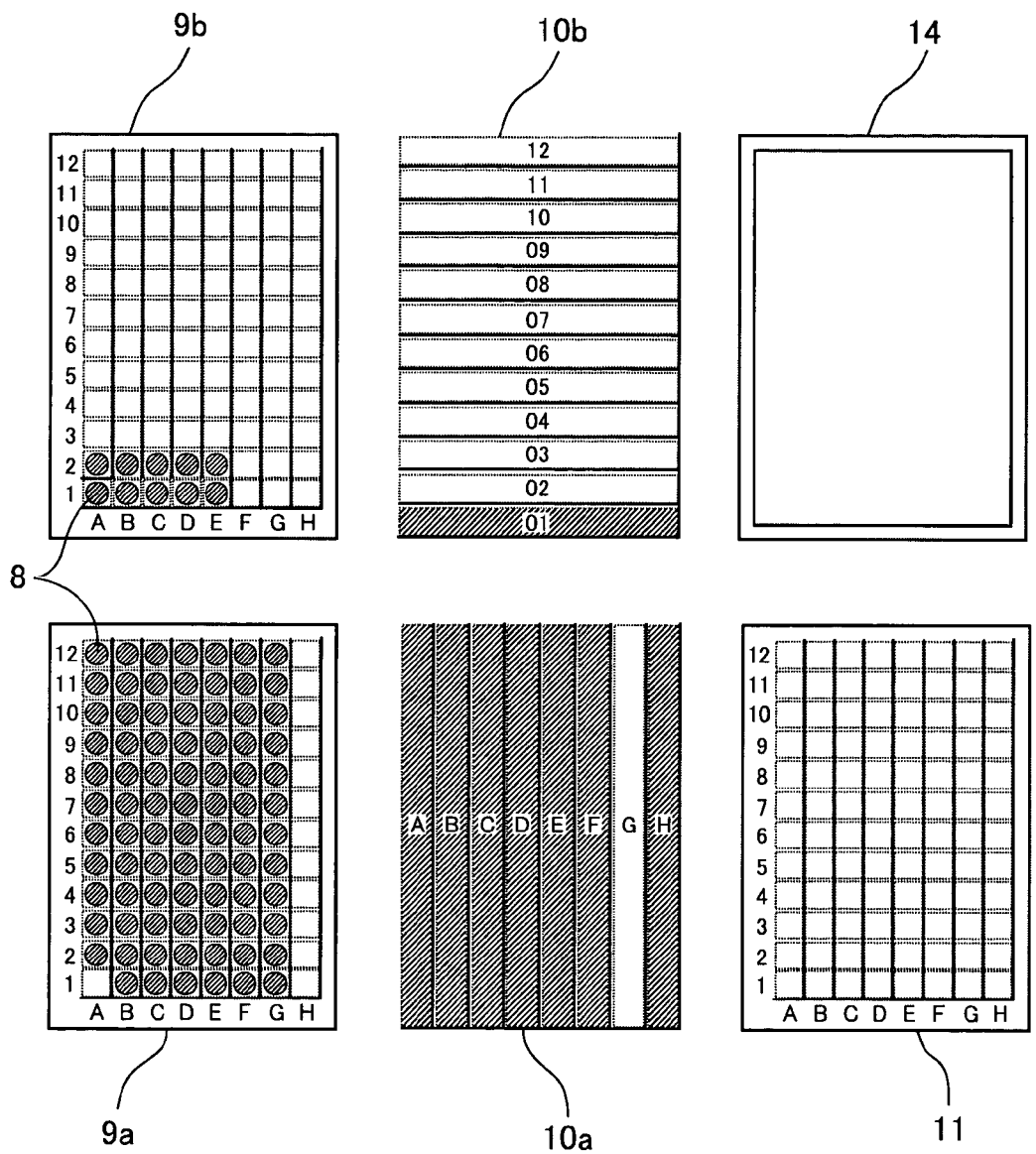
FIG. 2 is an explanatory diagram illustrating an arrangement of dispensing tip container, reagent container, microplate, and disposal container.

FIG. 2 shows an arrangement of each of the containers as viewed from above. In the arrangement shown in FIG. 2, dispensing tip containers 9a and 9b are disposed at the left side for holding the dispensing tips 8 arranged in an array. Reagent containers 10a and 10b are disposed at the center, and the microplate 11 and the disposal container 14 are disposed at the right side. The area for holding reagent in the reagent container 10a is divided into columns "A" to "H". Also the area for holding reagent in the reagent container 10b is divided into rows "1" to "12". Different reagents can be dispensed into each row or column of reagent containers 10a and 10b. When the dispensing head 6 is in such an orientation that the lengthwise direction of the head 6 is in coincidence with the direction in which the column extends, the dispensing tip container 9a and reagent container 10a are used. When the dispensing head 6 is swiveled 90 degrees and the lengthwise direction thereof is in coincidence with the direction in which the row extends, then the dispensing tip container 9b and reagent container 10b are used. The disposal container 14 is sufficiently large for disposing of the used dispensing tips regardless of whether the dispensing head 6 is oriented in the direction of column or row. The arrangement shown in FIG. 2 is only an example, and the arrangement of containers can be freely changed to suit the requirements of the experiment. However, it is necessary to input and save information regarding the arrangement of containers to the control device in advance.

When carrying out reagent reaction experiments, the reagent is normally refrigerated. In this embodiment, a cooling device 12 is disposed below the reagent containers 10a and 10b, as shown in FIG. 1, to maintain the reagent at, for example, 4° C. Also, in order to shake the microplate 11 after reagent is dispensed into the microplate 11, the microplate 11 is placed on a shaker 13 and is shook thereby while maintaining a fixed temperature. This operation is referred to as incubating.

The control device 3 controls the robot 5 to bring the dispensing head 6 to the desired position, and controls the dispensing head 6 to execute liquid sucking in or expelling operations. Also, the process (protocol) of a reagent reaction experiment, such as that shown in FIG. 3, can be input to the control device 3. For inputting the process to the control device 3, a keyboard 17 or a mouse 18 is used.

Figure 3:
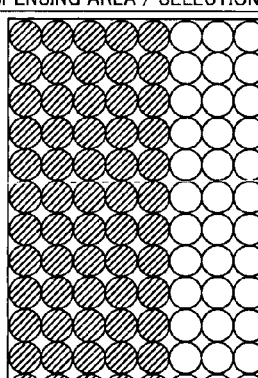
FIG. 3 shows an example of the screen for creating the process and timers according to an embodiment of the present invention.

FIG. 3 shows an example of an input screen for inputting the process. When inputting the process, one process to be executed is selected from an edit menu 32, and the process is transferred to a process column 33. For example, if dispense is selected from the edit menu 32 and transferred to the process column 33, an information input screen 34 appears for inputting all the information needed for the dispense operation. With the information input screen 34, various kinds of information can be input including reagent 37 to be selected, the dispense quantity 3B, the range of dispense destination wells 35, and dispense direction 36. For example, the symbol → means to carry out dispense operations in the direction from column "A" toward column "H" in the microplate 11. Also, the symbol ↑ means to carry out dispense operations in the direction from row "1" toward row "12" of the microplate 11.

The right side of FIG. 3 shows an information input screen 34 for a process from incubate to dispensing stop solution. The information input screen 34 includes a time setting portion 30 for setting a period of time before the stop solution is dispensed (hereinafter referred to as "predetermined period of time"). The range of wells in the microplate 11 into which stop solution is to be dispensed can be specified on an individual basis or on a row or a column basis. Furthermore, the control device 3 includes timers 31 for measuring a period of time from immediately after reagent is dispensed into each row or column of the microplate 11. When the control device 3 is executing a process, the control device 3 compares the period of time measured by the timer 31 with the predetermined period of time. The dispense reaction stop solution operation will not be executed before the measured period of time has reached the set period of time.

The control device 3 includes a self-determination function 40. The self-determination function 40 can simulate the time to execute the processes input in advance for a reagent reaction experiment, and determine whether the automatic liquid handling system 1 can execute the operations in the time specified at the time setting portion 30, and inform the operator of the result.

Figure 5:
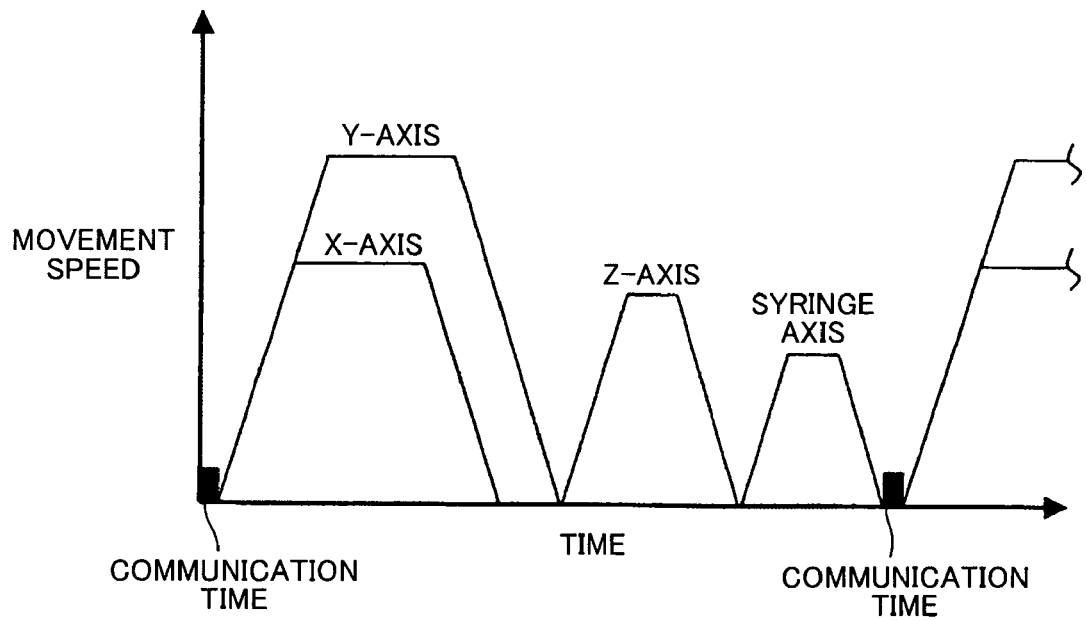
FIG. 5 is a graphical representation showing movement of a robot.

Next, the self-determination function will be described. As described above, an operator prepares a process table of the processes that are to be executed, such as the table shown in FIG. 6. The processes are input to the control device 3. The control device 3 has a function for calculating the actual time required from the processes input. For example, the robot 5 is moved in accordance with a trapezoid acceleration/deceleration pulse train, so the movement and dispense time can be calculated from the predetermined acceleration or deceleration, maximum speed, traveling distance, etc. Naturally, when several axes are moving simultaneously, it is the axis with the longest movement time that is selected. In the example shown in FIG. 5, the robot 5 is firstly moved along the X- and Y-axes simultaneously at the same speed. When positioning of the Y-axis is determined, the robot 5 is moved in the direction of Z-axis. That is, the robot 5 is moved to a predetermined height. Then, the syringe axis is driven in order to suck in or expel reagent into or out of the dispensing tips 8. The times for these movements are calculated. Because each is movement is controlled by the control device 3, data transmission time needs to be taken into consideration to obtain the total time required for executing all the operations. It is possible to calculate the data transmission time from the amount of data and the transmission speed. It is therefore possible to simulate the time required for each process by summing the time required to execute each operation in the process and the data transmission time. For example, in the case of process number 1 in FIG. 6, the time required to attach the dispensing tips, suck in the reagent 1 and dispense the reagent in the microplate 11, dispose the dispensing tips 8 in the disposal container 14, and the time required to transmit the commands for each of these operations can be calculated and summed. The result of summing these times is the time required to execute process number 1. In this way, as shown in the "Time Required" column of FIG. 6, the control device 3 can calculate the time required to execute each process.

Figure 4:
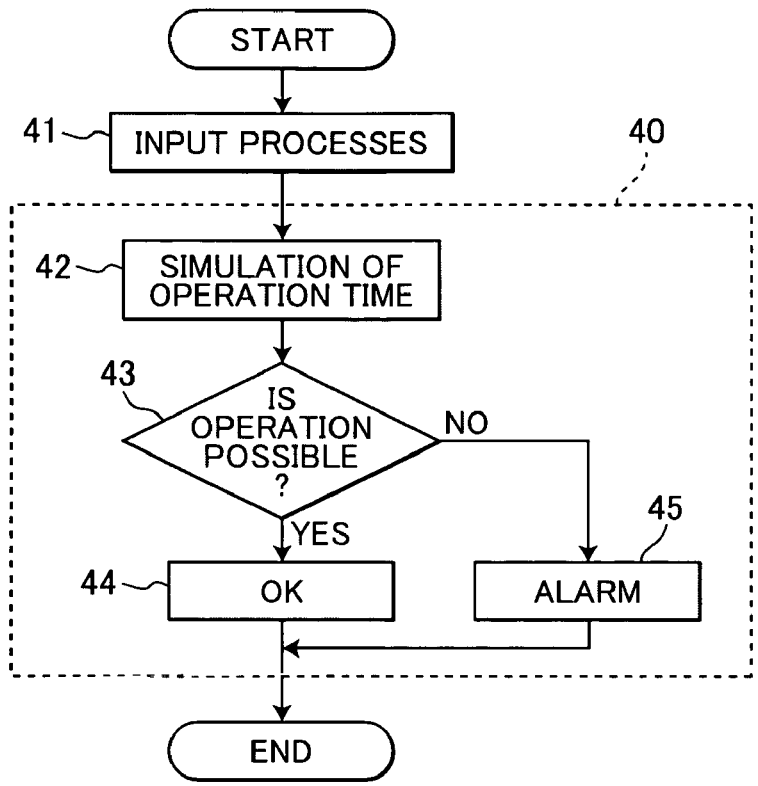
FIG. 4 is a flowchart showing the self-determination function of an embodiment of the present invention.

The self-determination function 40 of the control device 3 determines whether the calculated operation time is in accordance with the required time input at the time setting 30, and informs the operator. Specifically, as shown in the flowchart in FIG. 4, the self-determination function 40 is executed after inputting the processes (step 41). First, the operation time simulation is executed (step 42). Then, the procedure determines whether the processes can be completed within the time input at the time setting 30 (step 43). If it is possible to execute the processes within the time input at the time setting 30, then the message "OK" is output to the screen (step 44). If it is not possible, then "Alarm" is displayed (step 45) to alert the operator that it is not possible to execute the processes within the time input at the time setting 30.

During the simulation, in accordance with the progress of the experiment, it is possible to display on the screen the status of use of the dispensing tips 8, the status of use of reagent, the status of dispensing in the microplate 11, using for example colors, symbols, or letters. In this way, the operator can accurately grasp the status of the simulation. This kind of display can be carried out not only during the simulation, but also during actual execution of the processes.

The following is an explanation of the actual operation, using the processes shown in FIG. 6 as an example. Firstly, the operator adds by hand 6 μl of the test specimen to wells A to E of row 1 of the microplate 11 in advance. The microplate 11 is placed on the shaker 13, and the door is closed. Then, the operator starts the processes input to the control device 3.

In process number 1, the automatic liquid handling system 1 attaches the five dispensing tips 8 set in the dispensing tip container 9b in columns "A" to "E" of row "1". Next, 144 μl of reagent in the reagent container 10b is sucked in, and dispensed in wells in columns "A" to "E" of row "1" of the microplate 11 placed on the shaker 13. The amplitude of shaking of the shaker 13 is about +/−1 mm, which is sufficiently small compared with the diameter of the wells, 8 mm. Therefore, even during incubation operations, dispensing operations can be carried out. After dispensing operations are completed, the dispensing tips 8 are disposed of in the disposal container 14 in order to avoid contamination.

In process number 2, the automatic liquid handling system 1 attaches the eleven dispensing tips 8 set in column "A", rows "2" to "12" of dispensing tip container 9a. Before this operation, the dispensing head 6 is rotated through 90 degrees. Then, 100 μl of reagent 2 in "A" of reagent container 10a is sucked in, and dispensed in wells "2" to "12" of column "A" of the microplate 11 placed on top of the shaker 13. Then, 100 μl of reagent 2 in "A" of reagent container 10a is again sucked in, and dispensed to wells "2" to "12" of column "B". This operation is repeated until the operation in column "E" is executed, and the dispensing tips 8 are disposed of to the disposal container 14.

The rotation of the dispensing head can be accomplished using, for example, a stepper motor or a solenoid or other type of actuator. Alternatively, a disk can be provided on the dispensing head, and an abutment member provided on the main body 2 of the automatic liquid handling system 1, so that the abutment member is capable of contacting the disk on the dispensing head 6. While the disk is contacting the abutment member, the dispensing head 6 is moved in the X or the Y-axis, causing the dispensing head 6 to rotate. The axis of rotation of the dispensing head 6 corresponds to the center of the dispensing head 6, For the dilution operation in process number 3, firstly the dispensing head is rotated and the dispensing tips 8 set in row "2", columns "A" to "E" of dispensing tip container 9b are attached to the dispensing head 6. The dispensing head 6 moves to row "1" of the microplate 11 on top of the shaker 13, and dips the dispensing tips 8 into the liquid in wells "A" to "E" of row "1". An agitation operation consisting of sucking in and expelling out the liquid is repeated five times. Then, 50 μl of liquid is sucked in, and 50 μl is dispensed into the neighboring wells "A" to "E" of row "2". This liquid is sucked in and expelled out five times. In the same way, 50 μl from row "2" is dispensed into row "3", then agitated and diluted. This type of operation is repeated until row "8". The dispensing tips 8 are disposed of in the disposal container 14 together with the 50 μl of liquid sucked in from row "8". In this process, diluted test specimen is generated in row "1" to "8" of the microplate 11.

In process number 4, an incubation operation is carried out by shaking the microplate 11 for 10 minutes at a fixed temperature, for example 37° C. The control device 3 executes the following process after the 10 minutes incubation time is complete.

Process numbers 5 to 9 are processes for dispensing reagent into the wells of columns "A" to "E" of microplate 11. The following is an explanation of how timers A to E provided for each column of microplate 11 measure the time from dispensing reagent.

In process number 5, the dispensing head rotates through 90 degrees to be oriented in the direction of column A, and attaches the dispensing tips 8 set in rows "1" to "12" of column B of the dispensing tip container 9a to the dispensing head 6. Next, 100 μl of reagent 3 contained in B of reagent container 10a is sucked in, and dispensed to wells "1" to "12" of column "A" of the microplate 11 on top of the shaker 13. Immediately after this, the control device 3 causes the timer A to clear to 0 and start counting up. Timer A counts up in units of one millisecond, for example. After dispensing, the twelve dispensing tips 8 are disposed of in the disposal container 14.

In process number 6, similar to process number 5, 100 μl of reagent 4 contained in "C" of reagent container 10a is sucked in, and dispensed to wells "1" to "12" of column B of the microplate 11. Immediately after this, the control device 3 causes the timer B to clear to 0 and start counting up.

Thereafter, similar processes are executed until process number 9, with reagents 5 to 7 being dispensed to columns "C" to "E" of the microplate 11, and timer C, timer D, and timer E started.

The time required for each dispensing operation is 50 seconds. Therefore, timer B is 50 seconds later than timer A, and timer C is 50 seconds later than timer 3, and similarly for timers D and E.

In process number 10, the microplate 11 in which reagent has been dispensed is incubated for 30 minutes at 37° C., following which 75 μl of stop solution is dispensed into columns "A" to "E" of the microplate 11. Firstly, dispensing tips 8 from column "G" of dispensing tip container 9a are attached to the dispensing head 6. Then, 75 μl of reagent, which is reaction stop solution, in column "H" of reagent container 10a is sucked in. The incubation operation is executed while comparing the desired reaction time input at the time setting 30, in other words 30 minutes or 1,800 seconds, with the time on the timer A. When the time on timer A reaches the 1,800 seconds, reagent 8 is dispensed into column "A" of the microplate 11. After dispensing, reagent is again sucked in, and the dispensing head waits at column B of the microplate 11. When timer B reaches 1,800 seconds, reagent B is dispensed into column B. Thereafter, similar operations are executed until reagent is dispensed into column "E" and reagent reactions are stopped in each of columns "A" to "E". The control device 3 measures the time on timers A to E, in other words, the time from immediately after reagent is dispensed until the time when stop solution is dispensed. This time can be displayed on the screen, or recorded to a memory medium or printer not shown on the drawings. The position where the dispensing head waits for the reaction time to be complete is not necessarily above the wells, but a suitable position would be where even if drops of the stop solution sucked into the dispensing tips 8 fell from the dispensing tips 8, they would cause no obstruction to the experiment. Also, stop solution for which temperature control is critical, and whose temperature would change to the ambient temperature if left standing in the dispensing tips 8, can be sucked from column "H" of the reagent container 10a just before the end of the reaction time.

The subsequent operations consist of the operator removing the microplate 11, and measuring the fluorescence intensity of the reaction products using a fluorescent plate reader (not shown).

The time setting 30 described above is provided in the "Incubate→Dispense stop solution" information input screen 34. However, an information input screen 34 for processes dispensing reagent for which time control is important can also be provided. A timer 31 is provided for measuring the time from dispensing the reaction start reagent for every column of the microplate 11, so it can be easily understood that an operation similar to the one described above can be performed.

In the processes taken as an example and described above, the time until dispensing the stop solution was 30 minutes. However, if this time were, for example, three minutes, then the time would finish during the time between executing process number 5 and process number 9. In this case, the self-diagnosing function 40 described above would simulate the actual process time for the processes created, and confirm whether the operations were possible or not. In other words, the self-determination function would determine whether, for example, during the time from start of process number 5 to the time of dispensing the stop solution, there was sufficient time to execute another process.

Also, in the process examples described above, the reaction time for the different reagents was set to the same duration. However, it is also possible to carry out experiments where the same reagent is added to the test specimen, and different times are provided for each column. In this case, after dispensing to the range of wells for the reagent, the time set at "Incubate→Dispense Stop solution" will be different for each column. In this kind of experiment, even if a fault should occur in the equipment during execution of a process or for some reason it becomes necessary to stop the equipment, then because the timer 31 will have measured the actual time from immediately after dispensing the reagent until the stop solution was dispensed, use can be made of the test results for the experiment.

In the embodiment of the present invention described above, an example was given where dispensing tips 8 were disposed of. However, fixed tips that are cleaned can also be used. Also, a microplate 11 with 96 wells was used as an example in the description. However, the present invention can also be easily applied to a dispensing head 6 for microplates 11 for smaller quantities with 384 wells or 1,536 wells.

What is claimed is:

1. An automatic liquid handling system comprising:
    a dispensing tip container having a plurality of holding portions for holding a plurality of dispensing tips;
    a dispensing head having attachment portions to which at least one dispensing tip selected from the plurality of dispensing tips is attached, wherein when one or more dispensing tips are attached to the attachment portions, the dispensing head is capable of performing sucking and expelling operations for sucking liquid in or expelling the liquid out from the one or more dispensing tips;
    moving means for moving the dispensing head;
    a reagent container that holds at least one reagent;
    a microplate formed with a plurality of wells for holding specimen;
    a control device that controls the sucking and expelling operations performed by the dispensing head and also controls the moving means to control movements of the dispensing head, the control device having input means for inputting one or more processes to be executed by the dispensing head; and
    time measuring means for measuring time starting from dripping the reagent into selected wells on the microplate by the expelling operation performed by the dispensing head and triggering dispensing a stop solution at a predetermined time based on the measuring.

2. The automatic liquid handling system according to claim 1, further comprising time setting means for setting a time to finish the one or more processes to be executed by the dispensing head.

3. The automatic liquid handling system according to claim 2, wherein the plurality of wells formed in The microplate is arranged in a matrix form defined by rows and columns, and the time measuring means comprises a plurality of timers, each of the plurality of timers being provided for each of the rows and each of the columns of the plurality of wells for enabling measurement of time on a row or a column basis.

4. The automatic liquid handling system according to claim 3, wherein the control device performs the expelling operation to drip another reagent into selected wells of the microplate when the time measuring means has measured a predetermined period of time.

5. The automatic liquid handling system according to claim 1, further comprising a display that indicates the time measured by the time measuring means.

6. The automatic liquid handling system according to claim 1, further comprising storage means for storing the time measured by the time measuring means.

7. An automatic liquid handling system comprising:
a dispensing tip container having a plurality of holding portions for holding a plurality of dispensing tips;
a dispensing head having attachment portions to which at least one dispensing tip selected from the plurality of dispensing lips is attached, wherein when one or more dispensing tips are attached to the attachment portions, the dispensing head as capable of performing sucking and expelling operations for sucking liquid in or expelling the liquid out from the one or more dispensing tips;
moving means for moving the dispensing head;
a reagent container that holds at least one reagent;
a mircoplate formed with a plurality of wells for holding specimen;
a control device that controls the sucking and expelling operations performed by the dispensing head and also controls the moving means to control movements of the dispensing head, the control device having input means for inputting one or more processes to be executed by the dispensing head; and
self-diagnosing means for simulating time to execute the one or more processes to be executed by the dispensing head and determining whether the one or more processes are executable within a predetermined time.

8. The automatic liquid handling system according to claim 7, wherein the self-diagnosing means comprises informing means for informing an operator of a result of determination.

9. The automatic liquid handling system of claim 7, wherein the predetermined time is related to a sum total of processing times for a plurality of wells.

10. An automatic liquid handling system comprising:
a dispensing tip container having a plurality of holding portions for holding a plurality of dispensing tips, the holding portions being arranged in a matrix form defined by rows and columns;
a dispensing head having attachment portions to which a plurality of dispensing tips are attached, wherein when dispensing tips are attached to the attachment portions, the dispensing head is capable of performing sucking and expelling operations for sucking liquid in or expelling the liquid out from the dispensing tips;
moving means for moving the dispensing head;
a reagent container having a plurality container portions for storing a reagent and having a plurality container portions for storing a reaction stop solution;
a microplate formed with a plurality of wells for holding specimen, the wells being arranged in a matrix form defined by rows and columns;
a control device that controls the sucking and expelling operations performed by the dispensing head and also controls the moving means to control movements of the dispensing head, wherein the control device includes input means for inputting one or more processes to be executed by the dispensing head, time selling means for setting a period of time between introduction of the reagent into a row or a column of the microplate and introduction of the reaction stop solution into the row or the column of the microplate; and
time measuring means for measuring a period of time starting from the reagent is dispensed into the row or the column of the microplate so that a dispense reaction will not be stopped before the measured period of time has reached the set period of time.

11. The automatic liquid handling system according to claim 10, wherein said time measuring means comprises a plurality of timers, each of the plurality of timers being provided for each of the columns of the plurality of wells of the microplate for enabling measurement of time on a column basis.

12. The automatic liquid handling system according to claim 10, wherein the time measuring means comprises a plurality of timers, each of the plurality of timers being provided for each of the rows of the plurality of wells for enabling measurement of time on a row basis.

13. The automatic liquid handling system according to claim 10, wherein the control device controls to dispense another reagent into selected wells of the microplate when the time measuring means has measured a predetermined period of time.

14. The automatic liquid handling system according to claim 10, further comprising a display that indicates the time measured by the time measuring means.

15. The automatic liquid handling system according to claim 10, further comprising storage means for storing the time measured by the time measuring means.

16. An automatic liquid handling system comprising:
a dispensing tip container having a plurality of holding portions for holding a plurality of dispensing tips;
a dispensing head having attachment portions to which at least one dispensing tip selected from the plurality of dispensing tips is attached, wherein when one or more dispensing tips are attached to the attachment portions, the dispensing head is capable of performing sucking and expelling operations for sucking liquid in or expelling the liquid out from the one or more dispensing tips;
moving means for moving the dispensing head;
a reagent container that holds at least one reagent;
a microplate formed with a plurality of wells for holding specimen; and
a control device that controls the sucking and expelling operations performed by the dispensing head and also controls the moving means to control movements of the dispensing head, wherein the control device includes input means for inputting one or more processes executed by the dispensing head, simulation means for calculating a period of time required for executing the one or more processes, judging means for determining whether the one or more processes can be performed within a predetermined period of time, and display means for indicating an alarm if the calculated period of time for executing the one or more processes exceeds the predetermined period of time.

* * * * *